(12) United States Patent
Hwang et al.

(10) Patent No.: US 6,337,190 B1
(45) Date of Patent: Jan. 8, 2002

(54) D-AMINO ACID AMINOTRANSFERASE FOR SIMULTANEOUSLY PRODUCING GLUTARYL-7-AMINOCEPHALOSPORANIC ACID AND D-AMINO ACID

(75) Inventors: Tzann-Shun Hwang; Szu-Pei Wu; Hsin-Hua Chou; Hwa-Yi Chen; Lung-Shen Lin; Hsin Tsai; Edward Chang, all of Taipei (TW)

(73) Assignee: Development Center for Biotechnology (TW)

( * ) Notice: Subject to any disclaimer, the term of this patent is extended or adjusted under 35 U.S.C. 154(b) by 0 days.

(21) Appl. No.: 09/466,257

(22) Filed: Dec. 17, 1999

(51) Int. Cl.$^7$ ............................. C12N 9/00; C12N 9/10
(52) U.S. Cl. ........................ 435/47; 435/183; 435/15; 435/69.1; 435/106
(58) Field of Search ........................ 435/47, 15, 69.1, 435/183, 193, 106

(56) References Cited

U.S. PATENT DOCUMENTS 4,745,061 A  5/1988 Aretz et al. .................. 435/193

OTHER PUBLICATIONS

Tanizawa, K. et al, *J. Biol. Chem*, 264:2445–2449, 1989.
Ian, G. F. et al., *J. of Bacterioloby*, 180:4319–4323, 1998.
Thorne et al., *J. Bacteriol*. 69: 357–362, 1954.
Thorne, C. B. and D. M. Molner, *J. Bacteriol*. 70, 420–426, 1955.
Hug, D. H. et al., *Arch. Biochem.Biophys*. 72, 369–375, 1957.
Gosling, J. P. et al., *Biochim. Biophys. Acta*, 522, 84–95, 1978.
Pucci, M. J. et al., *J. Bacterol*. 177, 336–342, 1995.
Merola, M. et al., *Biochemistry* 28, 505–509, 1989.
Jones et al., *Method Enzymol*. 113, 108–113, 1985.
Yagi et al. *Anal. Biochem*. 110, 146–149, 1981.

*Primary Examiner*—Rebecca E. Prouty
*Assistant Examiner*—Manjunath N. Rao
(74) *Attorney, Agent, or Firm*—Morgan & Finnegan, LLP (57) ABSTRACT

The present invention relates to mutant D-amino acid aminotransferase, including nucleic acids encoding mutant D-amino acid aminotransferase. The mutant D-amino acid aminotransferase of the present invention is obtained by the substitution of the glutamate residue at position 13 of wild type D-amino acid aminotransferase from *Bacillus sphaericus* with hydrophobic amino acids. The mutant D-amino acid aminotransferase can be used in the production of D-amino acid and the conversion of glutaryl-7-aminocephalosporanic acid from cephalosporin C. The present invention also includes replica-paper staining method for screening the cells expressing high DAT activity.

6 Claims, 6 Drawing Sheets

```
-133  AAGCTTCACACGCCAAGCACTTCACTGAAAAATCTACTTTGATTTACTGCATCTGGTCTT
 -73  ACTTGATCGTCTAGTCGGAATCATTGTACTTAAAAATGTGAAAATAACTTAAAAATGAAA
 -13  AGGATGTATAAACATGGCATACTCATTATGGAATGACCAAATCGTTGAAGAAGGATCTAT
  +1              M  A  Y  S  L  W  N  D  Q  I  V  E  E  G  S  I
  47  TACAATTTCACCAGAAGACCGTGGTTATCAATTTGGTGATGGTATTTACGAAGTAATCAA
  17   T  I  S  P  E  D  R  G  Y  Q  F  G  D  G  I  Y  E  V  I  K
 107  AGTATATAACGGGCATATGTTTACAGCACAAGAGCACATCGATCGTTTCTATGCTAGTGC
  37   V  Y  N  G  H  M  F  T  A  Q  E  H  I  D  R  F  Y  A  S  A
 167  CGAAAAAATTCGCCTTGTTATTCCTTATACAAAAGATGTATTACACAAATTATTGCATGA
  57   E  K  I  R  L  V  I  P  Y  T  K  D  V  L  H  K  L  L  H  D
 227  TTTAATCGAAAAAAATAATTTAAATACAGGTCATGTTTACTTCCAAATTACACGTGGAAC
  77   L  I  E  K  N  N  L  N  T  G  H  V  Y  F  Q  I  T  R  G  T
 287  AACTTCTCGTAACCACATTTTCCCCGGATGCAAGCGTACCAGCAGTGCTAACAGGTAATGT
  97   T  S  R  N  H  I  F  P  D  A  S  V  P  A  V  L  T  G  N  V
 347  TAAAACTGGTGAACGTTCAATTGAAAATTTCGAAAAAGGCGTAAAAGCGACATTGGTTGA
 117   K  T  G  E  R  S  I  E  N  F  E  K  G  V  K  A  T  L  V  E
 407  AGATGTTCGTTGGTTACGTTGTGATATTAAATCTTTAAATTTACTTGGCGCGGTACTTGC
 137   D  V  R  W  L  R  C  D  I  K  S  L  N  L  L  G  A  V  L  A
 467  GAAACAAGAAGCATCTGAAAAAGGTTGTTACGAAGCCATTTTACACCGTGGAGATATTAT
 157   K  Q  E  A  S  E  K  G  C  Y  E  A  I  L  H  R  G  D  I  I
 527  CACAGAATGTTCTTCTGCTAATGTCTATGGTATTAAAGATGGTAAACTTTATACGCACCC
 177   T  E  C  S  S  A  N  V  Y  G  I  K  D  G  K  L  Y  T  H  P
 587  AGCAAATAACTACATCTTAAATGGTATTACACGCCAAGTTATATTAAAATGTGCCGCTGA
 197   A  N  N  Y  I  L  N  G  I  T  R  Q  V  I  L  K  C  A  A  E
 647  AATAAATTTACCAGTGATTGAAGAGCCGATGACAAAAGGCGATTTATTAACAATGGATGA
 217   I  N  L  P  V  I  E  E  P  M  T  K  G  D  L  L  T  M  D  E
 707  AATTATTGTGTCTTCTGTTTCATCTGAAGTGACACCGGTTATCGATGTGGATGGTCAGCA
 237   I  I  V  S  S  V  S  S  E  V  T  P  V  I  D  V  D  G  Q  Q
 767  AATTGGTGCAGGTGTTCCTGGTGAATGGACTCGTAAATTGCAAAAAGCATTTGAGGCAAA
 257   I  G  A  G  V  P  G  E  W  T  R  K  L  Q  K  A  F  E  A  K
 827  ATTACCAATTTCAATTAATGCCTAATCTGTATAAATGATTAAAAAGAGCTACCTAAAACT
 277   L  P  I  S  I  N  A  *
 887  TGGTTATTCGCCAAGTTAGGAGGGTAGCTCTTTTTTTATAGAACAAAATATGCATGTATTC
 947  TCCTGAAACGTCATGTAAAATAAAAAAGATAGCGCCTTTAGTCGATATCACGGTGATACC
1007  GACTAGTAACGAGGCGAATTTGATATGGGGCAGTAAGATTGGAGTGACCTAAAC
```

*The underlined codons are the start codon and stop codon.

FIG.3

```
-133  AAGCTTCACACGCCAAGCACTTCACTGAAAAATCTACTTTGATTTACTGCATCTGGTCTT
 -73  ACTTGATCGTCTAGTGGGAATCATTGTACTTAAAAATGTGAAAATAACTTAAAAATGAAA
 -13  AGGATGTATAAACATGGCATACTCATTATGGAATGACCAAATCGTTGAAGTAGGATCTAT
  +1            M  A  Y  S  L  W  N  D  Q  I  V  E  V  G  S  I
  47  TACAATTTCACCAGAAGACCGTGGTTATCAATTTGGTGATGGTATTTACGAAGTAATCAA
  17   T  I  S  P  E  D  R  G  Y  Q  F  G  D  G  I  Y  E  V  I  K
 107  AGTATATAACGGGCATATGTTTACAGCACAAGAGCACATCGATCGTTTCTATGCTAGTGC
  37   V  Y  N  G  H  M  F  T  A  Q  E  H  I  D  R  F  Y  A  S  A
 167  CGAAAAAATTCGCCTTGTTATTCCTTATACAAAAGATGTATTACACAAATTATTGCATGA
  57   E  K  I  R  L  V  I  P  Y  T  K  D  V  L  H  K  L  L  H  D
 227  TTTAATCGAAAAAAATAATTTAAATACAGGTCATGTTTACTTCCAAATTACACGTGGAAC
  77   L  I  E  K  N  N  L  N  T  G  H  V  Y  F  Q  I  T  R  G  T
 287  AACTTCTCGTAACCACATTTTTCCCGGATGCAAGCGTACCAGCAGTGCTAACAGGTAATGT
  97   T  S  R  N  H  I  F  P  D  A  S  V  P  A  V  L  T  G  N  V
 347  TAAAACTGGTGAACGTTCAATTGAAAATTTCGAAAAAGGCGTAAAAGCGACATTGGTTGA
 117   K  T  G  E  R  S  I  E  N  F  E  K  G  V  K  A  T  L  V  E
 407  AGATGTTCGTTGGTTACGTTGTGATATTAAATCTTTAAATTTACTTGGCGCGGTACTTGC
 137   D  V  R  W  L  R  C  D  I  K  S  L  N  L  L  G  A  V  L  A
 467  GAAACAAGAAGCATCTGAAAAAGGTTGTTACGAAGCCATTTTACACCGTGGAGATATTAT
 157   K  Q  E  A  S  E  K  G  C  Y  E  A  I  L  H  R  G  D  I  I
 527  CACAGAATGTTCTTCTGCTAATGTCTATGGTATTAAAGATGGTAAACTTTATACGCACCC
 177   T  E  C  S  S  A  N  V  Y  G  I  K  D  G  K  L  Y  T  H  P
 587  AGCAAATAACTACATCTTAAATGGTATTACACGCCAAGTTATATTAAAATGTGCCGCTGA
 197   A  N  N  Y  I  L  N  G  I  T  R  Q  V  I  L  K  C  A  A  E
 647  AATAAATTTACCAGTGATTGAAGAGCCGATGACAAAAGGCGATTTATTAACAATGGATGA
 217   I  N  L  P  V  I  E  E  P  M  T  K  G  D  L  L  T  M  D  E
 707  AATTATTGTGTCTTCTGTTTCATCTGAAGTGACACCGGTTATCGATGTGGATGGTCAGCA
 237   I  I  V  S  S  V  S  S  E  V  T  P  V  I  D  V  D  G  Q  Q
 767  AATTGGTGCAGGTGTTCCTGGTGAATGGACTCGTAAATTGCAAAAAGCATTTGAGGCAAA
 257   I  G  A  G  V  P  G  E  W  T  R  K  L  Q  K  A  F  E  A  K
 827  ATTACCAATTTCAATTAATGCCTAATCTGTATAAATGATTAAAAAGAGCTACCTAAAACT
 277   L  P  I  S  I  N  A  *
 887  TGGTTATTCGCCAAGTTAGGAGGGTAGCTCTTTTTTTATAGAACAAAATATGCATGTATTC
 947  TCCTGAAACGTCATGTAAAATAAAAAAGATAGCGCCTTTAGTCGATATCACCGTGATACC
1007  GACTAGTAACGAGGCGAATTTGATATGCGGCAGTAAGATTGGAGTGACCTAAAC
```

*The underlined codons are the start codon and stop codon.

D-AMINO ACID AMINOTRANSFERASE FOR SIMULTANEOUSLY PRODUCING GLUTARYL-7-AMINOCEPHALOSPORANIC ACID AND D-AMINO ACID

BACKGROUND OF THE INVENTION

1. Field of the Invention

The present invention relates to a D-amino acid aminotransferase mutant, a nucleic acid sequence encoding such enzyme mutant, an expression vector containing such nucleic acid sequence, the preparation of such enzyme mutant and the use thereof. The invention also provides a method for selecting clones with high D-amino acid aminotransferase activity.

2. Description of the Related Prior Art

D-amino acid aminotransferase (DAT) is widely used in the transamination reaction and the production of D-amino acid. DAT has high stereoselectivity and can convert one amino acid to another in the presence of a pyridoxal or pyridoxamine phosphate and an alpha-keto acid corresponding to the amino acid to be produced.

DATs from various sources have been isolated and characterized. DAT was firstly found in the extracts of *Bacillus subtillis* by Thorne et al., (1954), J. Bacteriol. 69: 357–362. Subsequently, DAT was demonstrated in bacteria of the genera Bacillus (Tanizawa, K. et al., (1989), J. Biol. Chem. 264, 2445–2449; Thorne, C. B. and D. M. Molnar, (1955), J. Bacteriol. 70, 420–426), *Rhodospirillum rubrum* (Hug, D. H. et al., (1957) Arch. Biochem.Biophys. 72, 369–375), *Rhizobium japonicum* (Gosling, J. P. et al., (1978) Biochim. Biophys. Acta 522, 84–95), and *Staphylococcus haemolyticus* (Pucci, M. J. et al., (1995) J. Bacteriol. 177, 336–342), higher plants and mammalian livers.

A D-amino acid aminotransferase has been isolated from *Bacillus sphaericus*. The enzyme has a molecular weight about 60 kDa and consists of two identical subunits. The encoding gene was isolated, sequenced and cloned into the plasmid pIF1001 and transformed into *E. coli* to express the enzyme (Ian G. F. et al., (1998), Journal of Bacteriology, P. 4319–4323). The optimum pH for the reaction of the *Bacillus sphaericus* D-amino acid aminotransferase is 8.5.

D-amino acid aminotransferase is useful for producing various D-amino acids which can be used in industrial or pharmaceutical products such as sweeteners, antibiotics, peptide enzymes and peptide hormones. For example, Alitame, tyrocidin A, antinomycin D, penicillin N and cephalosporin C, and cyclosporin A comprise D-alanine and D-phenylalanine, D-valine, D-alpha amino valerate, D-alpha aminoavalerate and D-alanine, respectively. Short peptides can also be capped with D-form amino acid to prevent digestion by protease and slow down enzymatic degradation. It is disclosed in U.S. Pat. No. 4,745,061 that *Bacillus lichiformis* has two aminotransferase: D-aminoacid transaminase and cephalosporin C aminotransferase. As shown in column 1 of the patent, the D-aminoacid transaminase is not capable of converting cephalosporin C. The cephalosporin C aminotransferase can be used in the conversion of cephalosporin C (Ceph C) to Glutaryl-7-aminocephalosporanic acid (GL-7ACA) which is a highly valuable pharmaceutical chemical for the synthesis of cephem antibiotics.

SUMMARY OF THE INVENTION

One objective of the invention is to provide a mutant D-amino acid aminotransferase which can simultaneously produce Glutaryl-7-aminocephalosporanic acid and D-amino acid.

Another objective of the invention is to provide a nucleic acid compound encoding the mutant D-amino acid aminotransferase of the invention, an expression vector comprising said nucleic acid and a host cell transformed with said vector.

The invention also provides a method for selecting clones with high D-amino acid aminotransferase activity.

BRIEF DESCRIPTION OF THE DRAWINGS

FIG. 3 shows the sequences of dat gene and the D-amino acid aminotransferase from *Bacillus sphaericus* (SEQ ID NOS: 7 and 8).

FIG. 4 shows the sequences of mutated dat gene and the mutant D-amino acid aminotransferase from *Bacillus sphaericus* (SEQ. ID NOS: 9 and 10).

DETAILED DESCRIPTION OF THE INVENTION

In the first aspect, the present invention provides a D-amino acid aminotransferase mutant, which is obtained by the substitution of glutamate at position 13 of D-amino acid aminotransferase produced from *Bacillus sphaericus* with a different amino acid.

The D-amino acid aminotransferase of the invention exhibits a high activity in the production of D-amino acid and the conversion of Ceph C to GL-7ACA. The present invention uses error-prone PCR (polymerase chain reaction) to mutate the dat gene of *Bacillus sphaericus*. Polymerase chain reaction is one of the most commonly used techniques for amplifying specific sequences. The reaction is performed by first isolating the target nucleic acid sequence from a biological sample, unwinding the two strands thereof, hybridizing the unwound strands with primers synthesized according to the sequences of the two ends of the target gene, and amplifying the target gene with DNA polymerase in the presence of suitable amounts of deoxynucleotide triphosphates such as dATP, dGTP, dCTP and dTTP. The difference between error-prone PCR and common PCR is that the error-prone PCR limits one of the four deoxynucleotide triphosphates to low amounts. The limited amounts of the deoxynucleotide triphosphates causes the mismatch of base pairs in the amplification. The parameters and reagents required for the reaction are all well known to persons skilled in the art. PCR can be performed stepwise and more commonly by commercially available automatic devices such as a DNA Thermal Cycler. Additionally, the oligonucleotide sequences used as the primers for PCR can be optionally modified in part, for example, to introduce the required endonuclease restriction sites and mutations. Such oligonucleotides can be readily designed and synthesized by methods known in the art. The template DNA is a single-stranded plasmid or phagmid containing the unmodified or native DNA sequences of the target DAT.

In a preferred embodiment, a suitable expression vector such as a plasmid or a phagemid containing the dat gene encoding DAT of *Bacillus sphaericus* is used as the template to perform error-prone PCR for mutating the dat gene.

Normally, the expression vector can be chosen by those skilled in the art as desired. The vectors can be transformed into a suitable host cell.

The invention also provides a replica paper-staining method for selecting the clones expressing high DAT activity, which comprises:
(a) replicating a transformed host cell onto a first filter paper;
(b) preparing a second filter paper containing an antibiotic and IPTG;
(c) covering the first filter paper with the second filter paper, and incubating both papers under suitable conditions;
(d) using chloroform vapor for the lysis of cells;
(e) preparing a developing paper by dipping a third filter paper into a reaction mixture containing D-aspartate, α-keto acid, Fast violet B and pyridoxal 5'-phosphate; and
(f) taping the first filiter paper to the developing paper for 3–5 minutes at room temperature, and selecting the colony with red color.

The replica paper-staining method is referred to as the activity staining method described by Merola, M. et al., (1989), Biochemistry 28, 505–509. Oxaloacetate-Fast violet B is used as the reagent to detect the clones with DAT activity. After the identification of the replica paper-staining method, mutant clones with high D-amino acid aminotransferase activity can be selected.

The nucleic acid sequences encoding the D-amino acid aminotransferase with high activity can be sequenced by an automatic system such as ABI PRISM Dye Terminator Cycle Sequencing Ready React Kit. By comparing with the wild type dat gene, the mutated position and the substituted amino acid can be determined. It is surprisingly found that the D-amino acid aminotransferase mutants having a substitution of glutamate at position 13 with a hydrophobic amino acid show high activity in the production of D-amino acid and the conversion of GL-7ACA from Ceph C. Preferably, said hydrophobic amino acids are alanine, valine, leucine, isoleucine, phenylalanine, tyrosine and tryptophan. More preferably, said hydrophobic amino acid is valine.

The wild dat gene and the mutated dat gene encoding D-amino acid aminotransferase with high activity were amplified by a primer and cloned into a plasmid. Plasmids containing the wild dat gene and the mutant dat gene obtained by the above method are then used respectively to transform suitable host cells and express the D-amino acid aminotransferase. Suitable host cells include bacteria *E. coli* or Bacillus, yeast, mammalian cells. Preferably, the bacterial expression system is used. Most preferably, the host is *E. coli*.

Protein expression is performed by processes well known in the art. Isolation of the protein product obtained yields a crude protein extract and further purification with conventional processes such as chromatography or acetone precipitation gives the refined protein.

D-amino acid aminotransferase activity assays are performed on the resultant enzyme mutants. The activity of D-amino acid aminotransferase can be measured by enzyme reaction such as NADH-dependent reduction reaction.

It is found that the D-amino acid aminotransferase based on the invention has a superior capability for producing glutaryl-7-aminocephalosporanic acid from cephalosporin C. The D-amino acid aminotransferase transfers D-amino group from cephalosporin C to pyruvate or α-ketoglutarate to generate keto-GL-7ACA and D-alanine or D-glutamate. The DAT activity against cephalosporin C is measured by HPLC analysis.

EXAMPLES

Example 1

Mutagenesis of dat Gene by Error-prone PCR

Preparation of Plasmids

Plasmids for cloning were prepared by the method as described by Sambrook et al. (1989), Molecular Cloning: a laboratory manual, and for sequencing were prepared by QIAprep Spin Plasmid Miniprep Kit.

Design of Primers

Two primers pTrcL and pTrcR (SEQ NOS: 5 and 6) were designed according to the sequence of plasmid pTrc99A. The other primers for sequencing or cloning were designed based on the sequence of dat gene from *Bacillus sphaericus* (Wang N. C., (1995), Master Thesis, Institute of Agricultural Chemistry, National Taiwan University). The sequences of primers were described in Table 1.

TABLE 1

Primers used for cloning and sequencing.

| Primers | | Application |
|---|---|---|
| DATAL-1 | (SEQ ID NO:1) 5'-TATAACCATGGCATACTCATTAT-3' | cloning |
| DATAR-3 | (SEQ ID NO:2) 5'-TTAGGAAGCTTTTTTTAATCATTTATAC-3' | cloning |
| DATAR-1 | (SEQ ID NO:3) 5'-GGGAAAATGTGGTTACGAG-3' | sequencing |
| DATAR-2 | (SEQ ID NO:4) 5'-TGTAGTTATTTGCTGGGTG-3' | sequencing |
| pTrc-L | (SEQ ID NO:5) 5'-GGCTCGTATAATGTGTGGAA-3' | sequencing |
| pTrc-R | (SEQ ID NO:6) 5'-GCTTCTGCGTTCTGATTTA-3' | sequencing |

PCR (Polymerase Chain Reaction) and Error-prone PCR

The reaction mixture for PCR contained 1 μl of template, 1 μl of each primer (100 pmole/μl), 8 μl of dNTPs (200 mM for each dNTP), 10 μl of 10 X polymerization buffer, 1 μl of Taq polymerase (2.5 U/μl) and 78 μl of deionized water. After mixing, 50 μl of mineral oil was added to cover the reaction mixture. The resulting solution was put into a RoboCycler Gradient-96 temperature cycler to perform PCR reaction in 30 cycles. The error-prone PCR was carried out as the same as for the PCR, except for limiting only one of the four deoxynucleotides to 20 mM in the reaction mixture.
Cloning of the Mutated dat Gene into Plasmid pTrc99A Plasmid pTrc99A and the dat gene fragment amplified under error-prone PCR by using primers DATAL-1 and DATAR-3 (SEQ ID NOS: 1 and 2) were digested with NcoI and HindIII, and ligated by T4 DNA ligase at 16° C. for 5 hours. The ligated DNAs were transformed into *E. coli* DH5α. The resulting transformants were subjected to the replica paper-staining assay method to select the clones with high DAT activity.

Plate Assay

Figure 1:
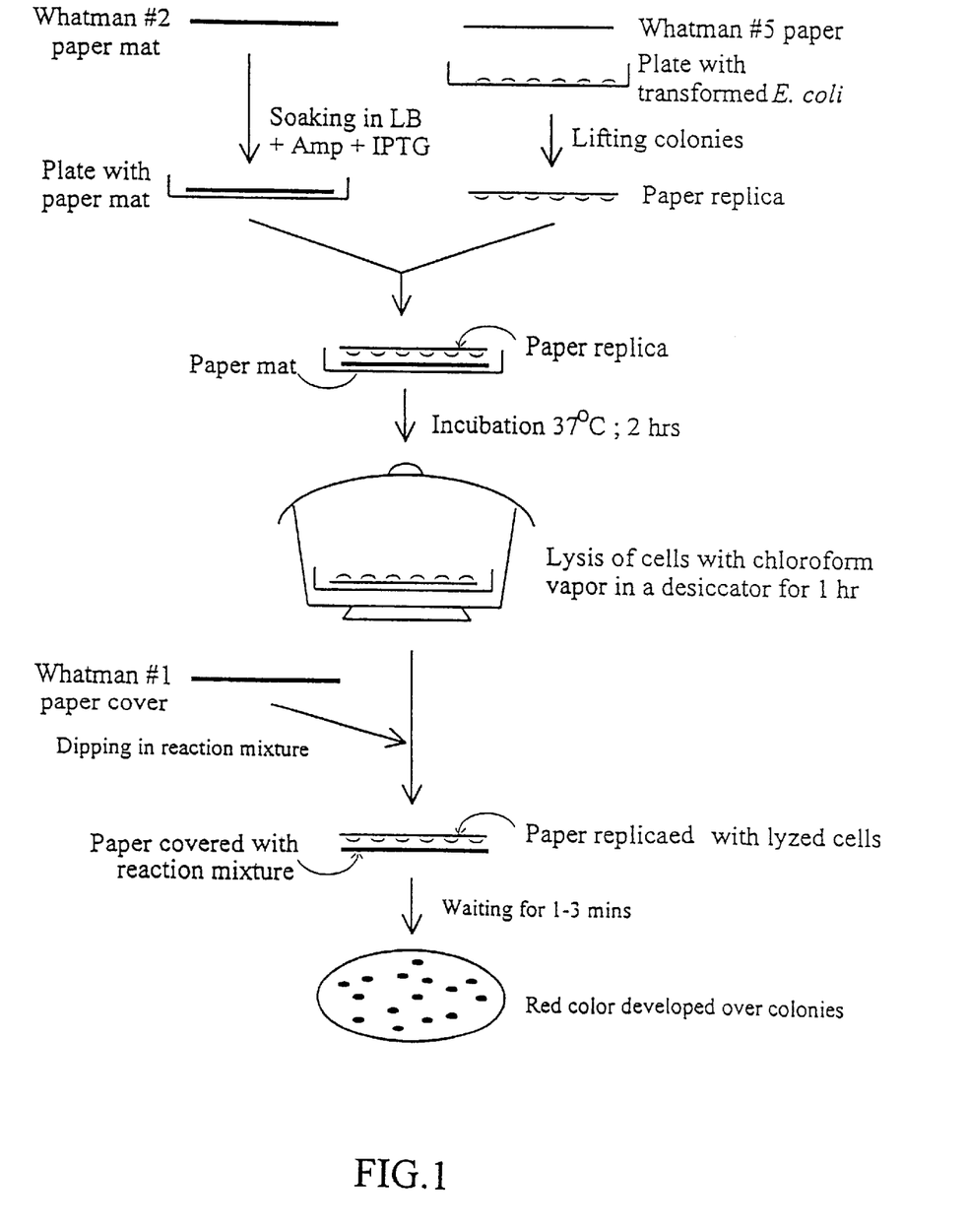
FIG. 1 shows the scheme of replica-paper staining assay.

The principle of the assay was based on the activity-staining method described as Merola et al. (1989), Biochemistry 28, 505–509. A plate assay method named as replica-paper staining assay was developed by applying the Oxaloacetate-Fast violet B colorimetric method (FIG. 1). Firstly, the *E. coli* cells were replicated onto a Whatman No.5 filter paper by pasting it to a plate containing the *E. coli* cells and then lifting the paper from the plate. The Whatman No.2 filter paper containing ampicillin (1,000 μg/ml) and IPTG (2 mM) was used to cover the paper with *E. coli* cells and then incubated at 37° C. for 2 hours for induction. Chloroform vapor was introduced to treat the filter paper for the lysis of the *E. coli* cells. The chloroform on the paper is vaporized in a hood. The assay mixture contains 20 mM D-aspartate, 300 μM α-ketoglutarate, 0.12% Fast violet B and 0.2 mM pyridoxal 5'-phosphate in TrisHCl buffer (pH 7.6). The developing paper was made by dipping Whatman No.1 filter paper to the freshly prepared reaction mixture. The filter paper with the lyzed *E. coli* was tapped to the developing paper for 3–5 minutes at room temperature. If the cells have DAT activity, the area with a cell colony would gradually develop a pink to red color.

Cloning Wild dat and Mutated dat into Plasmid pKmA

Figure 2:
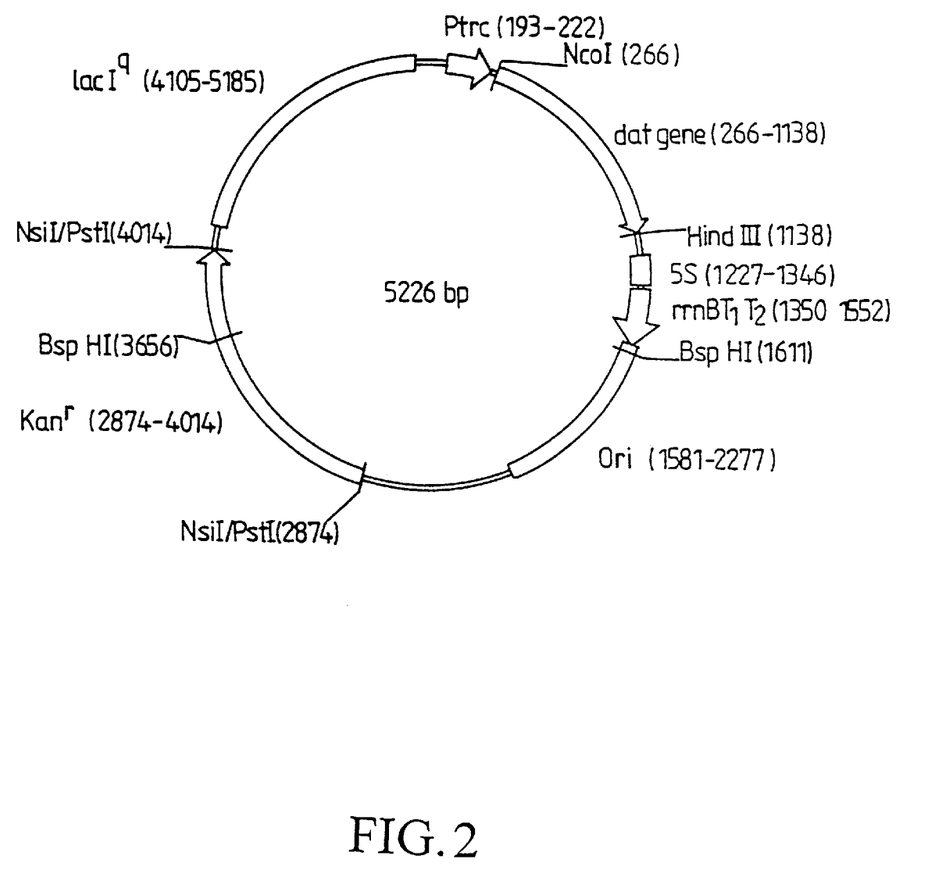
FIG. 2 shows the restriction map of plasmid pKmDAT and pKmM56.

The wild-type dat gene and mutated dat gene were amplified by 5' primer DATAL-1 and 3' primer DATAR-3 (SEQ ID NOS: 1 and 2), and then cloned into plasmid pKmA between NcoI site and HindIII site to generate plasmids pKmDAT and pKmM56, respectively (FIG. 2). Plasmids pKmDAT and pKmM56 were transformed into *E. coli* DH5α. The transformants were cultivated at Luria-Bertani medium with 50 μg/ml of kanamycin for enzyme assay.

Sequence Analysis of Mutated dat Gene

Sequencing reaction was carried out by ABI PRISM Dye Terminator Cycle Sequencing Ready Reaction Kit. The reaction mixture contains 8 μl of terminator ready reaction mix, 0.5 μg of double-stranded DNA, 3.2 pmole of primer and distilled water to adjust the mixture to 20 μl in total. The resulting solution was covered with one drop of mineral oil. The PCR reaction was cycled 20 times. After the reaction was completed, the solution was rolled on the parafilm membrane to eliminate the mineral oil and ethanol was added to precipitate the DNAs. The resulting pellet DNA was resuspended by a loading buffer comprising deionized formamide and 25 mM EDTA (pH 8.0) containing 50 mg/ml Blue dextran in a ratio of 5:1. The solution was analyzed by the ABI 373 autosequencer.

The sequence of the wild-type dat gene and amino acid are shown in FIG. 3 (SEQ ID NOS 7 and 8). Sequence analysis of the clone with high DAT activity shows that the *E. coli* DH5α/pTrcM56 has a single mutation at E13V in the dat gene wherein the glutamate at position 13 is substituted with valine. The sequence of the mutated dat gene and amino acid of the invention is shown in FIG. 4 (SEQ ID NOS: 9 and 10).

Example 2

Enzyme Assay

The activity of DAT was measured by coupling the NADH-dependent reduction reaction (Jones et al., (1985), Method Enzymol. 113, 108–113; Yagi et al. (1981), Anal. Biochem. 110, 146–149). The reaction mixture contains 0.1 M TrisHCl (pH 8.3), 25 mM D-alanine or D-aspartate, 25 mM α-ketoglutarate, 0.1 mM NADH, 2.0 U L-lactic dehydrogenase for D-alanine or malate dehydrogenase for D-aspartate, and the crude extract. The mixture is measured by the decrease in absorbance at 340 nm for 2–3 minutes at room temperature. When using D-alanine as a substrate, one unit was defined as the amount of enzyme that produced the pyruvate equal to 1 μmole NADH consumed for converting pyruvate to lactate per minute at room temperature. When using D-aspartate as a substrate, one unit is defined as the amount of enzyme that produced the oxaloacetate equal to 1 μmole NADH consumed for converting oxaloacetate to malate per minute at room temperature.

After analysis of the clones by the plate assay, we selected the most active clone as *E. coli* DH 5α/pTrcM56. The DAT activity of *E. coli* DH 5α harboring pTrcM56 was about 51.3 U/mg when using D-alanine and α-ketoglutarate as substrate and about 9.6 U/mg when using D-aspartate and α-ketoglutarate as substrate (Table 2).

TABLE 2

The DAT activity in *E. coli* DH5α harboring pTrc-DAT and pTrc-M56

| Substrates | | Specific activity (U/mg) | |
|---|---|---|---|
| Amino donor | Amino accepter | pTrcDAT | pTrcM56 |
| D-alanine[a] | α-ketoglutarate | 23.68 | 51.30 |
| D-aspartate[b] | α-ketoglutarate | 5.43 | 9.63 |

[a]One unit is defined as the amount of enzyme that produces the pyruvate equal to 1 μmole NADH consumed for converting pyruvate to lactate per minute at room temperature.
[b]One unit is defined as the amount of enzyme that produces the oxaloacetate equal to 1 μmole NADH consumed for converting oxaloacetate to malate per minute at room temperature.

Example 3

HPLC Analysis of the DAT Activity Against Ceph C

HPLC analysis of the DAT activity against Ceph C was performed by the method modified from Lee et al., 1994, Biotechnol. Lett. 16:467–472. The reaction mixture contained 12.5 mM Ceph C, 12.5 mM pyruvate or α-ketoglutarate and appropriate crude extracts in 0.1 M TrisHcl buffer, pH 8.3 in a final volume of 1 ml. The mixture was incubated at 37° C. for 10 minutes and then added to 60 μl of 3% hydrogen peroxide for reacting at 37° C. for 10 minutes. The products of the bioconvertion in the supernatant were then analyzed by HPLC. The mobile phase was 10% methanol in 0.2 M ammonium acetate buffer (pH 4.8). A Spherisorb S5 ODS2 column (250 mm ×4.6 mm, Phase separations Ltd, U.K.) was used and the UV detector was set at 260 nm. The retention times for Ceph C and GL-7ACA at a flow rate of 1 ml/min were 5.6 minutes and 13.5 minutes, respectively. By using Ceph C as a substrate, one unit was defined as the amount of enzyme that produced 1 μmole GL-7ACA per minute at 37° C.

Figure 5:
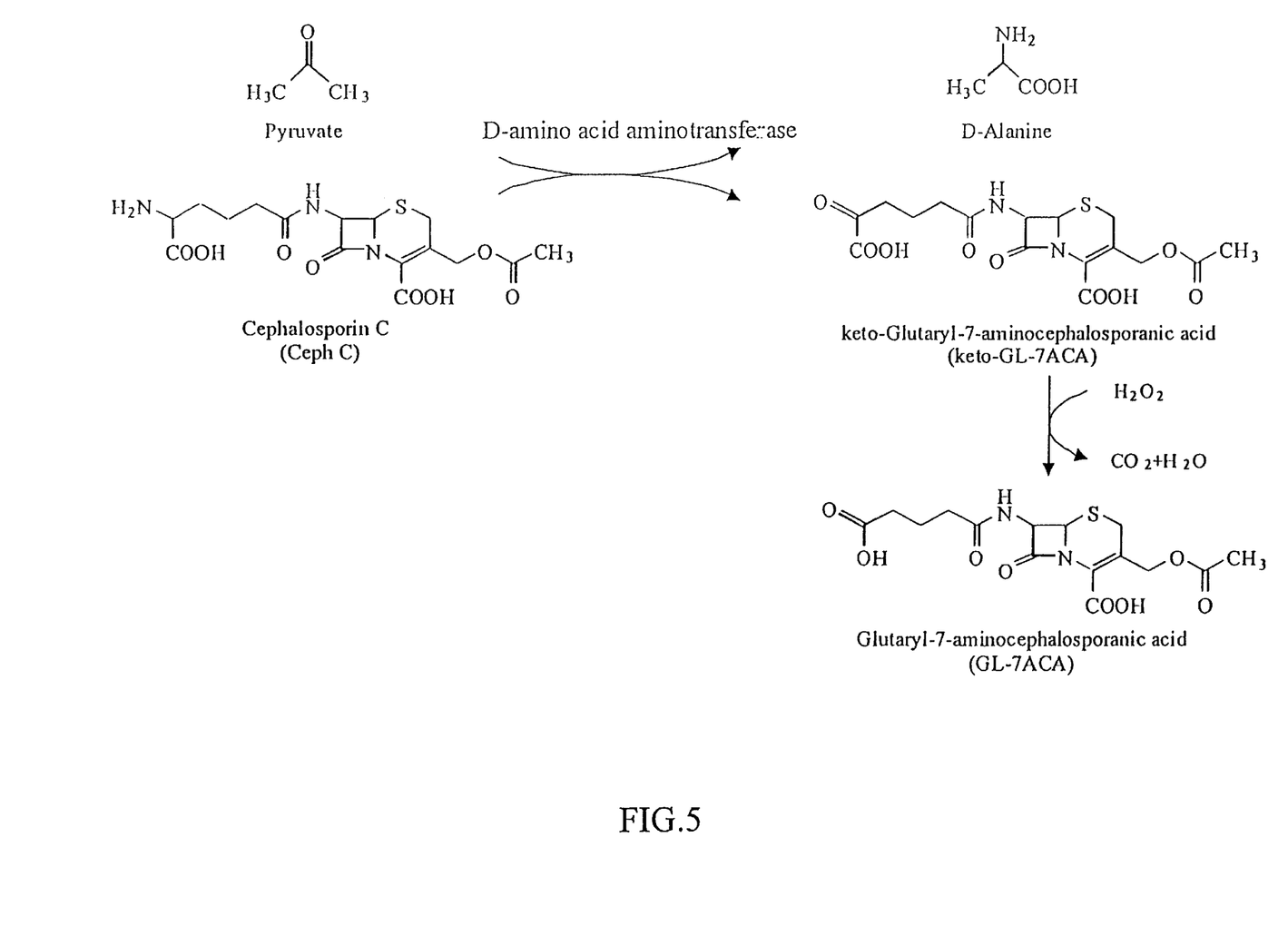
FIG. 5 shows the scheme of the production of GL-7ACA by using D-amino acid aminotransferase.

HPLC analysis showed that DAT could be used to produce GL-7ACA. The D-amino group were transferred from Ceph C to pyruvate or α-ketoglutarate by DAT to generate keto-GL-7ACA and D-alanine or D-glutamate. The keto GL-7ACA further reacted with hydrogen peroxide to generate GL-7ACA. The biosynthesis diagram of GL-7ACA is shown in FIG. 5. By using Ceph C and α-ketoglutarate as substrates, *E. coli* DH5α harboring pKmDAT and pKmM56 could respectively have activity of 1.1 U/mg and 1.6 U/mg. By using Ceph C and pyruvate as substrates, *E. coli* DH5α harboring pKmDAT and pKmM56 could respectively have activities of 0.94 U/mg and 1.58 U/mg (Table 3).

TABLE 3

The DAT activity in *E. coli* DH5α harboring pKm-DAT and pKm-M56

| Substrates | | Specific activity (U/mg) | |
|---|---|---|---|
| Amino donor | Amino accepter | pKmDAT | pKmM56 |
| D-alanine[a] | α-ketoglutarate | 19.20 | 29.62 |
| Cephalosporin C[b] | α-ketoglutarate | 1.12 | 1.68 |
| Cephalosporin C[b] | pyruvate | 0.94 | 1.58 |

[a]One unit is defined as the amount of enzyme that produces the pyruvate equal to 1 μmole NADH consumed for converting pyruvate to lactate per minute at room temperature.
[b]One unit is defined as the amount of enzyme that produces 1 μmole GL-7ACA per minute at 37° C.

Figure 6:
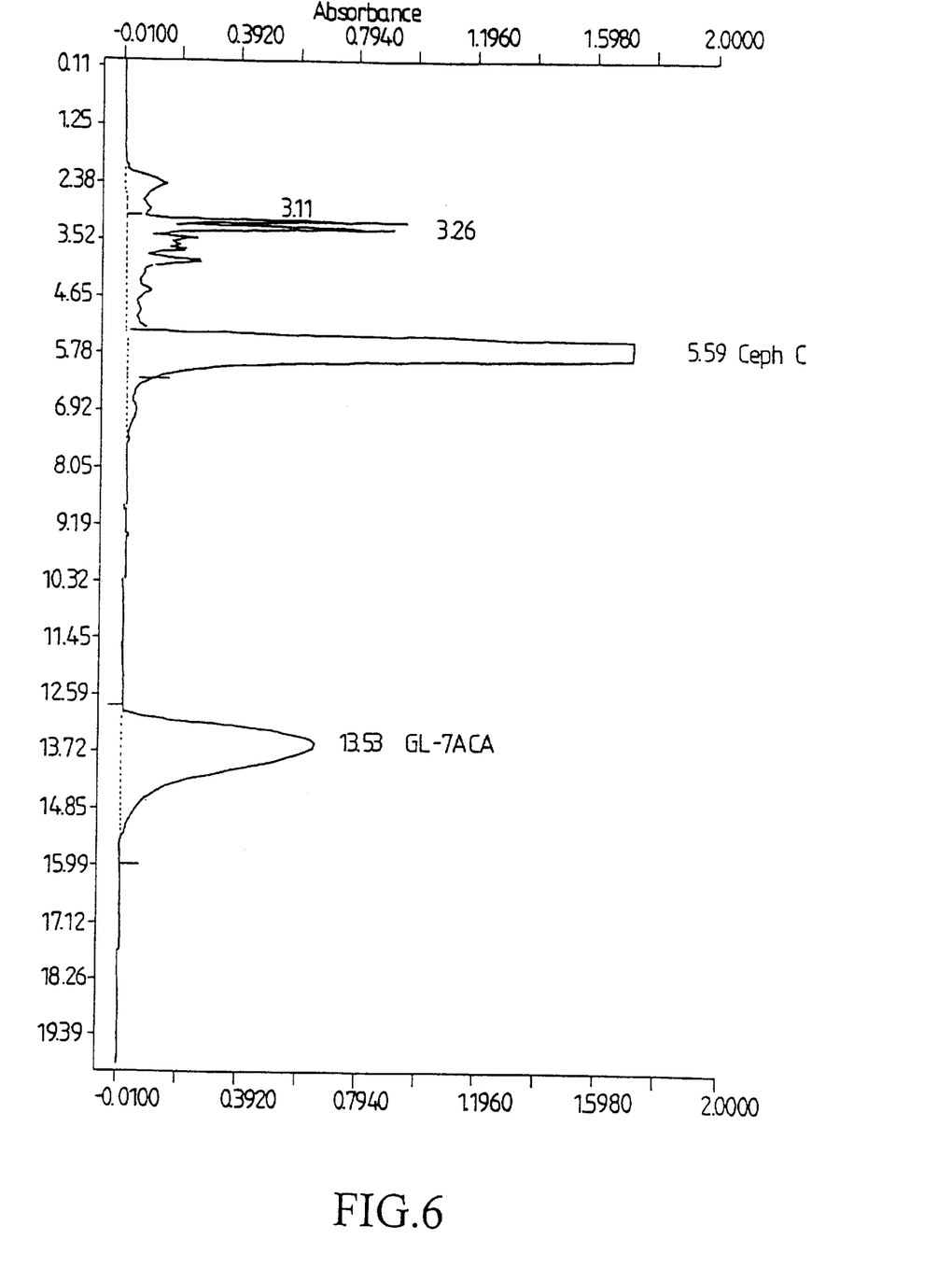
FIG. 6 shows HPLC chromatography of GL-7ACA from the conversion of cephalosporin C by using D-amino acid aminotransferase.

FIG. 6 shows that the conversion of GL-7ACA from cephalosporin C can be measured by HPLC. The productivity for GL-7ACA of the *E. coli* harboring wild or mutant DAT was analyzed. Using D-alanine and α-ketoglutarate as substrates, the productivity of *E. coli* harboring pKmDAT and pKmM56 were, respectively, 121,340 U/l and 178,020 U/l. Using Ceph C and α-ketoglutarate as substrates, the productivity of *E. coli* harboring pKmDAT was 7,610 U/l and that of pKmM56 was 10,480 U/l. Using Ceph C and pyruvate as substrates, the productivity of *E. coli* harboring pKmDAT and pKmM56 were, respectively, 6,390 U/l and 9,920 U/l (Table 4).

TABLE 4

The productivity of DAT in *E. coli* DH5α harboring pKm-DAT and pKm-M56

| Substrates | | Productivity ($\times 10^3$ U/l) | |
|---|---|---|---|
| Amino donor | Amino acceptor | pKmDAT | pKmM56 |
| D-alanine[a] | α-ketoglutarate | 121.34 | 178.02 |
| Cephalosporin C[b] | α-ketoglutarate | 7.61 | 10.48 |
| Cephalosporin C[b] | pyruvate | 6.39 | 9.92 |

[a]One unit is defined as the amount of enzyme that produces pyruvate equal to 1 μmole NADH consumed for converting pyruvate to lactate per minute at room temperature.
[b]One unit is defined as the amount of enzyme that produces 1 μmole GL-7ACA per minute at 37° C.

We claim:

1. A mutant D-amino acid aminotransferase, which is obtained by the substitution of glutamate at position 13 of D-amino acid aminotransferase, SEQ ID NO: 8, from *Bacillus sphaericus* with a different amino acid.

2. The mutant D-amino acid aminotransferase of claim 1, wherein the different amino acid is a hydrophobic amino acid.

3. The mutant D-amino acid aminotransferase of claim 1, wherein the hydrophobic amino acid is selected from the group consisting of alanine, valine, leucine, isoleucine, phenylalanine, tyrosine and tryptophan.

4. The mutant D-amino acid aminotransferase of claim 3, wherein the hydrophobic amino acid is valine.

5. A method of making the D form of an amino acid by using the mutant D-aminotransferase of claim 1, 2, 3 or 4 in the production of the D-amino acid, the steps comprising:

a) adding a mutant D-amino acid transferase of claims 1, 2, 3 or 4 as an enzyme to a substrate mixture comprising an amino donor, a first D-amino acid and an amino acceptor, a first keto-acid to form a second D-amino acid and a second keto-acid; and b) isolating the product a second D-amino acid and a second keto-acid.

6. A method of producing Glutaryl-7-aminocephalosporanic acid from Cephalosporin C by using the mutant aminotransferase of claim 1, 2, 3, or 4 as an enzyme, the steps comprising:

a) adding a mutant D-amino acid transferase of claims 1, 2, 3 or 4 as an enzyme to a substrate mixture comprising Cephalosporin C and a D-amino acceptor selected from the group consisting of a pyruvate and an α-ketoglutarate to form keto-GL-7ACA and respectively D-Alanine and D-glutamate;

b) reacting the mixture with hydrogen peroxide; and c) isolating Glutaryl-7-aminocephalosporanic acid as a product.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: DATAL-1
      primer

<400> SEQUENCE: 1
tataaccatg gcatactcat tat                                           23

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:  DATAR-3
      primer

<400> SEQUENCE: 2
ttaggaagct tttttttaatc atttatac                                      28

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:  DATAR-1
      primer

<400> SEQUENCE: 3
gggaaaatgt ggttacgag                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: DATAR-2
      primer

<400> SEQUENCE: 4
tgtagttatt tgctgggtg                                            19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: pTrc-L
      primer

<400> SEQUENCE: 5
ggctcgtata atgtgtggaa                                           20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: pTrc-R
      primer

<400> SEQUENCE: 6
gcttctgcgt tctgattta                                            19

<210> SEQ ID NO 7
<211> LENGTH: 1194
<212> TYPE: DNA
<213> ORGANISM: Bacillus sphaericus

<400> SEQUENCE: 7
aagcttcaca cgccaagcac ttcactgaaa aatctacttt gatttactgc atctggtctt 60
acttgatcgt ctagtgggaa tcattgtact taaaaatgtg aaaataactt aaaaatgaaa 120
aggatgtata aacatggcat actcattatg gaatgaccaa atcgttgaag aaggatctat 180
tacaatttca ccagaagacc gtggttatca atttggtgat ggtatttacg aagtaatcaa 240
agtatataac gggcatatgt ttacagcaca agagcacatc gatcgtttct atgctagtgc 300
cgaaaaaatt cgccttgtta ttccttatac aaaagatgta ttacacaaat tattgcatga 360
tttaatcgaa aaaaataatt taaatacagg tcatgtttac ttccaaatta cacgtggaac 420
aacttctcgt aaccacattt tcccggatgc aagcgtacca gcagtgctaa caggtaatgt 480
taaaactggt gaacgttcaa ttgaaaattt cgaaaaaggc gtaaaagcga cattggttga 540
agatgttcgt tggttacgtt gtgatattaa atctttaaat ttacttggcg cggtacttgc 600
gaaacaagaa gcatctgaaa aaggttgtta cgaagccatt ttacaccgtg gagatattat 660
cacagaatgt tcttctgcta atgtctatgg tattaaagat ggtaaacttt atacgcaccc 720
agcaaataac tacatcttaa atggtattac acgccaagtt atattaaaat gtgccgctga 780
aataaattta ccagtgattg aagagccgat gacaaaaggc gatttattaa caatggatga 840
aattattgtg tcttctgttt catctgaagt gacaccggtt atcgatgtgg atggtcagca 900
aattggtgca ggtgttcctg gtgaatggac tcgtaaattg caaaaagcat ttgaggcaaa 960
attaccaatt tcaattaatg cctaatctgt ataaatgatt aaaaagagct acctaaaact 1020

```
tggttattcg ccaagttagg agggtagctc ttttttatag aacaaaatat gcatgtattc      1080
tcctgaaacg tcatgtaaaa taaaaaagat agcgccttta gtcgatatca cggtgatacc      1140
gactagtaac gaggcgaatt tgatatgggg cagtaagatt ggagtgacct aaac            1194
```

<210> SEQ ID NO 8
<211> LENGTH: 283
<212> TYPE: PRT
<213> ORGANISM: Bacillus sphaericus

<400> SEQUENCE: 8

```
Met Ala Tyr Ser Leu Trp Asn Asp Gln Ile Val Glu Glu Gly Ser Ile
 1               5                  10                  15

Thr Ile Ser Pro Glu Asp Arg Gly Tyr Gln Phe Gly Asp Gly Ile Tyr
            20                  25                  30

Glu Val Ile Lys Val Tyr Asn Gly His Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Asp Leu Ile Glu Lys
 65                  70                  75                  80

Asn Asn Leu Asn Thr Gly His Val Tyr Phe Gln Ile Thr Arg Gly Thr
                 85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
        115                 120                 125

Gly Val Lys Ala Thr Leu Val Glu Asp Val Arg Trp Leu Arg Cys Asp
    130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190

Tyr Thr His Pro Ala Asn Asn Tyr Ile Leu Asn Gly Ile Thr Arg Gln
        195                 200                 205

Val Ile Leu Lys Cys Ala Ala Glu Ile Asn Leu Pro Val Ile Glu Glu
    210                 215                 220

Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
                245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
        275                 280

<210> SEQ ID NO 9
<211> LENGTH: 1194
<212> TYPE: DNA
<213> ORGANISM: Bacillus sphaericus

<400> SEQUENCE: 9
aagcttcaca cgccaagcac ttcactgaaa aatctacttt gatttactgc atctggtctt     60
```

-continued

```
acttgatcgt ctagtgggaa tcattgtact taaaaatgtg aaaataactt aaaaatgaaa        120
aggatgtata aacatggcat actcattatg gaatgaccaa atcgttgaag taggatctat        180
tacaatttca ccagaagacc gtggttatca atttggtgat ggtatttacg aagtaatcaa        240
agtatataac gggcatatgt ttacagcaca agagcacatc gatcgtttct atgctagtgc        300
cgaaaaaatt cgccttgtta ttccttatac aaaagatgta ttacacaaat tattgcatga        360
tttaatcgaa aaaataatt taaatacagg tcatgtttac ttccaaatta cacgtggaac        420
aacttctcgt aaccacattt tcccggatgc aagcgtacca gcagtgctaa caggtaatgt        480
taaaactggt gaacgttcaa ttgaaaattt cgaaaaaggc gtaaagcga cattggttga        540 agatgttcgt tggttacgtt gtgatattaa atctttaaat ttacttggcg cggtacttgc        600
gaaacaagaa gcatctgaaa aaggttgtta cgaagccatt ttacaccgtg gagatattat        660
cacagaatgt tcttctgcta atgtctatgg tattaaagat ggtaaacttt atacgcaccc        720
agcaaataac tacatcttaa atggtattac acgccaagtt atattaaaat gtgccgctga        780
aataaattta ccagtgattg aagagccgat gacaaaaggc gatttattaa caatggatga        840
aattattgtg tcttctgttt catctgaagt gacaccggtt atcgatgtgg atggtcagca        900
aattggtgca ggtgttcctg gtgaatggac tcgtaaattg caaaaagcat ttgaggcaaa        960
attaccaatt tcaattaatg cctaatctgt ataaatgatt aaaaagagct acctaaaact       1020
tggttattcg ccaagttagg agggtagctc ttttttatag aacaaaatat gcatgtattc       1080
tcctgaaacg tcatgtaaaa taaaaagat agcgccttta gtcgatatca cggtgatacc       1140
gactagtaac gaggcgaatt tgatatgggg cagtaagatt ggagtgacct aaac            1194
```

<210> SEQ ID NO 10
<211> LENGTH: 283
<212> TYPE: PRT
<213> ORGANISM: Bacillus sphaericus

<400> SEQUENCE: 10

```
Met Ala Tyr Ser Leu Trp Asn Asp Gln Ile Val Glu Val Gly Ser Ile
  1               5                  10                  15

Thr Ile Ser Pro Glu Asp Arg Gly Tyr Gln Phe Gly Asp Gly Ile Tyr
             20                  25                  30

Glu Val Ile Lys Val Tyr Asn Gly His Met Phe Thr Ala Gln Glu His
         35                  40                  45

Ile Asp Arg Phe Tyr Ala Ser Ala Glu Lys Ile Arg Leu Val Ile Pro
     50                  55                  60

Tyr Thr Lys Asp Val Leu His Lys Leu Leu His Asp Leu Ile Glu Lys
 65                  70                  75                  80

Asn Asn Leu Asn Thr Gly His Val Tyr Phe Gln Ile Thr Arg Gly Thr
                 85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
        115                 120                 125

Gly Val Lys Ala Thr Leu Val Glu Asp Val Arg Trp Leu Arg Cys Asp
    130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175
```

-continued

```
Thr Glu Cys Ser Ser Ala Asn Val Tyr Gly Ile Lys Asp Gly Lys Leu
            180             185             190

Tyr Thr His Pro Ala Asn Asn Tyr Ile Leu Asn Gly Ile Thr Arg Gln
        195             200             205

Val Ile Leu Lys Cys Ala Ala Glu Ile Asn Leu Pro Val Ile Glu Glu
    210             215             220

Pro Met Thr Lys Gly Asp Leu Leu Thr Met Asp Glu Ile Ile Val Ser
225             230             235             240

Ser Val Ser Ser Glu Val Thr Pro Val Ile Asp Val Asp Gly Gln Gln
            245             250             255

Ile Gly Ala Gly Val Pro Gly Glu Trp Thr Arg Lys Leu Gln Lys Ala
            260             265             270

Phe Glu Ala Lys Leu Pro Ile Ser Ile Asn Ala
        275             280
```